(12) United States Patent
Zhou et al.

(10) Patent No.: US 11,504,133 B2
(45) Date of Patent: Nov. 22, 2022

(54) ATRIAL APPENDAGE CLIP

(71) Applicant: BEIJING MED ZENITH MEDICAL SCIENTIFIC CO., LTD., Beijing (CN)

(72) Inventors: Qingliang Zhou, Beijing (CN); Danian Ke, Beijing (CN); Jian Meng, Beijing (CN); Xiaofang Liu, Beijing (CN)

(73) Assignee: BEIJING MED ZENITH MEDICAL SCIENTIFIC CO., LTD., Beijing (CN)

( * ) Notice: Subject to any disclaimer, the term of this patent is extended or adjusted under 35 U.S.C. 154(b) by 565 days.

(21) Appl. No.: 16/322,935

(22) PCT Filed: Dec. 29, 2016

(86) PCT No.: PCT/CN2016/112823
§ 371 (c)(1),
(2) Date: Feb. 2, 2019

(87) PCT Pub. No.: WO2018/032691
PCT Pub. Date: Feb. 22, 2018

(65) Prior Publication Data
US 2019/0183510 A1 Jun. 20, 2019

(30) Foreign Application Priority Data
Aug. 16, 2016 (CN) .......................... 201610676751.4

(51) Int. Cl.
*A61B 17/122* (2006.01)
*A61B 17/128* (2006.01)
(52) U.S. Cl.
CPC ........ *A61B 17/1227* (2013.01); *A61B 17/122* (2013.01); *A61B 17/1285* (2013.01)

(58) Field of Classification Search
CPC combination set(s) only.
See application file for complete search history.

(56) References Cited

U.S. PATENT DOCUMENTS

| 8,568,430 B2 | 10/2013 | Shipp |
| 2004/0106980 A1* | 6/2004 | Solovay .................... A61F 2/07 623/1.13 |

(Continued)

FOREIGN PATENT DOCUMENTS

| CN | 203074795 U | 7/2013 |
| CN | 105193471 A | 12/2015 |

(Continued)

OTHER PUBLICATIONS

The extended European search report dated Mar. 3, 2020 re: Application No. 16913443.4, pp. 1-8.

(Continued)

*Primary Examiner* — Thomas Mcevoy
(74) *Attorney, Agent, or Firm* — Gang Yu (57) ABSTRACT

Disclosed is an atrial appendage clip, including a first clip arm and a second clip arm that are symmetrically arranged; a first cavity and a second cavity are correspondingly provided in the first clip arm and the second clip arm along an axial direction thereof; a first spring and a second spring are correspondingly provided in the first cavity and the second cavity; the first spring is connected with the second clip arm via a first pull wire, and the second spring is connected with the first clip arm via a second pull wire, so as to form a closed loop structure; and as the first spring and the second spring are stretched or compressed, the first clip arm and the second clip arm are opened or closed therebetween.

5 Claims, 4 Drawing Sheets

(56) References Cited

U.S. PATENT DOCUMENTS

| | | |
|---|---|---|
| 2006/0020271 A1 | 1/2006 | Stewart et al. |
| 2008/0039879 A1 | 2/2008 | Chin et al. |
| 2008/0208324 A1 | 8/2008 | Glithero et al. |
| 2012/0035622 A1 | 2/2012 | Kiser et al. |
| 2012/0035631 A1 | 2/2012 | Hughett, Sr. et al. |
| 2012/0109161 A1 | 5/2012 | Privitera et al. |
| 2013/0190777 A1 | 7/2013 | Hughett, Sr. et al. |
| 2015/0173767 A1 | 6/2015 | Monti et al. |
| 2015/0320426 A1 | 11/2015 | Cosgrove, III et al. |

FOREIGN PATENT DOCUMENTS

| | | | |
|---|---|---|---|
| CN | 106137302 A | | 11/2016 |
| CN | 206275717 U | | 6/2017 |
| EP | 1600108 A2 | | 11/2005 |
| JP | B46-027998 | | 8/1971 |
| JP | 2005334646 A | | 12/2005 |
| WO | 2007009099 A3 | | 6/2007 |
| WO | 2010011661 A1 | | 1/2010 |
| WO | WO 2015/095333 | * | 6/2015 |

OTHER PUBLICATIONS

JP first Office Action dated Dec. 9, 2019 re: Application No. 2019-505533, pp. 1-3.

* cited by examiner

ATRIAL APPENDAGE CLIP

RELATED APPLICATIONS

This application is a national phase entry under 35 U.S.C. § 371 of International Patent Application PCT/CN2016/112823, having an International filing date of Dec. 29, 2016, and which claims priority to Chinese Patent Application No. 201610676751.4, having a filing date of Aug. 16, 2016, both of which are incorporated herein by reference in their entirety.

TECHNICAL FIELD

Embodiments of the present disclosure relate to a technical field of medical appliances, and in particular to an atrial appendage clip.

BACKGROUND

Atrial fibrillation is one of the most common arrhythmias clinically. A cerebral stroke caused by the atrial fibrillation has a very serious consequence, with the death rate and the disability rate up to 70%. For a patient suffering from valvular atrial fibrillation, 57% of atrial thrombi are from a left atrial appendage. For a patient suffering from non-valvular atrial fibrillation, 90% of left atrial thrombi are from the left atrial appendage. Even though a sinus rhythm is restored, due to stunned shrinkage of the left atrial appendage, a thrombus may still be formed.

At present, three methods are provided mainly to clinically prevent an atrial fibrillation ischemic stroke. The first method is to take an anticoagulant drug such as warfarin. However, the warfarin has a hemorrhage risk and many contraindications and must be monitored frequently, and thus is difficult to put into a clinical application. Besides, it is possible for the warfarin to cause osteoporosis and soft tissue necrosis. The second method is to directly excise or ligate an atrial appendage during a heart surgery. A main defect of such a method is the low complete closure rate of the left atrial appendage, and it is shown in a previous study that the success rate for completely excising the left atrial appendage is about 80% at maximum. The third method is to close the left atrial appendage via an appliance and is a percutaneous interventional atrial appendage occlusion product; but such a method has a complex operation and a high risk, and the safety and the effectiveness are to be verified.

SUMMARY

(1) Technical Problems to be Solved

An objective of the present disclosure is to design an atrial appendage clip which is safe and effective, and is convenient to operate, so that the atrial appendage clip is placed from an outside of a heart to a root of a left atrial appendage to close the left atrial appendage in a thoracotomy or minimally invasive surgery.

(2) Technical Solutions

In order to solve the above technical problems, the present disclosure provides an atrial appendage clip, which includes a first clip arm and a second clip arm that are symmetrically arranged; a first cavity and a second cavity are respectively provided in the first clip arm and the second clip arm along an axial direction of the first clip arm and the second clip arm; a first spring and a second spring are respectively provided in the first cavity and the second cavity; the first spring is connected with the second clip arm by a first pull wire, and the second spring is connected with the first clip arm by a second pull wire, so as to form a closed loop structure; and as the first spring and the second spring are stretched or compressed, the first clip arm and the second clip arm are capable of being opened or closed.

In an exemplary embodiment, one end of the first spring is connected with an end wall of the first cavity, and the other end of the first spring is connected with a corresponding end of the second clip arm by the first pull wire; and one end of the second spring is connected with an end wall of the second cavity, and the other end of the second spring is connected with a corresponding end of the first clip arm by the second pull wire.

In an exemplary embodiment, two ends of the first spring are respectively connected to first pull wires; two ends of the second spring are respectively connected to second pull wires; the first pull wires are correspondingly connected with the second pull wires; or two ends of the first spring are fixedly connected with two ends of the second clip arm respectively by the first pull wires; and two ends of the second spring are fixedly connected with two ends of the first clip arm respectively by the second pull wires.

In an exemplary embodiment, a first wire passing through hole communicating with the first cavity is formed at one end of the first clip arm; the first pull wire is connected with the corresponding end of the second clip arm through the first wire passing through hole; a second wire passing through hole communicating with the second cavity is formed at one end of the second clip arm; and the second pull wire is connected with the corresponding end of the first clip arm through the second wire passing through hole.

In an exemplary embodiment, one end, far away from the first wire passing through hole, of the first clip arm is provided with a first plug; the first plug is configured to block a port of the first cavity; one end of the first spring is connected with an end portion of the first plug; one end, far away from the second wire passing through hole, of the second clip arm is provided with a second plug; the second plug is configured to block a port of the second cavity; and one end of the second spring is connected with an end portion of the second plug.

In an exemplary embodiment, one end, close to the first wire passing through hole, of the first clip arm is provided with a first fixed pulley; one end, close to the second wire passing through hole, of the second clip arm is provided with a second fixed pulley; the first pull wire is connected with the corresponding end of the second clip arm by the first fixed pulley; and the second pull wire is connected with the corresponding end of the first clip arm by the second fixed pulley.

In an exemplary embodiment, first wire passing through holes communicating the first cavity are respectively formed at two ends of the first clip arm; the first pull wires correspondingly pass through the first wire passing through holes; second wires passing through holes communicating the second cavity are respectively formed at two ends of the second clip arm; the second pull wires correspondingly pass through the second wire passing through holes; first fixed pulleys are respectively disposed at the two ends of the first clip arm; second fixed pulleys are respectively disposed at the two ends of the second clip arm; the first pull wires that respectively pass through corresponding first fixed pulleys are correspondingly connected with the second pull wires that respectively pass through corresponding second fixed pulleys; or the first pull wires that respectively pass through corresponding first fixed pulleys are connected with the two ends of the second clip arm; and the second pull wires that respectively pass through corresponding second fixed pulleys are connected with the two ends of the first clip arm.

In an exemplary embodiment, one end portion of the first clip arm is provided with a first mounting groove for mounting the first fixed pulley; and one end portion of the second clip arm is provided with a second mounting groove for mounting the second fixed pulley.

In an exemplary embodiment, end portions of the first clip arm are respectively provided with first mounting grooves for mounting the first fixed pulleys; and end portions of the second clip arm are respectively provided with second mounting grooves for mounting the second fixed pulleys.

In an exemplary embodiment, middle sleeves are respectively disposed out of the first clip arm and the second clip arm in a sleeving manner; and a plurality of radial cutting grooves are formed out of each of the middle sleeves.

In an exemplary embodiment, a protective sleeve knitted by a braided fabric is further respectively disposed out of the first clip arm and the second clip arm in a sleeving manner; and the braided fabric is spun by a Polyethylene Terephthalate (PET), a Polytetrafluoroethylene (PTFE), a Polypropylene (PP), a velvet, a Polyglutamic Acid (PGA) or a Propanediol (PDO).

(3) Beneficial Effects

Compared with the conventional art, the present disclosure has the following advantages.

According to the atrial appendage clip provided by the present disclosure, the first clip arm and the second clip arm that are arranged in parallel are adopted; the first cavity and the second cavity are correspondingly provided in the first clip arm and the second clip arm along the axial direction thereof; the first spring and the second spring are correspondingly provided in the first cavity and the second cavity; the first spring is connected with the second clip arm by the first pull wire, and the second spring is connected with the first clip arm by the second pull wire, so as to form the closed loop structure; under the action of an external force, as the first spring and the second spring are stretched or compressed, the first clip arm and the second clip arm are capable of being opened or closed therebetween; with the design of arranging the springs in the clip arms, the outline dimension of the atrial appendage clip is reduced, and extrusion and abrasion to a peripheral tissue of an atrial appendage are reduced; moreover, with the increase in the thickness of the atrial appendage, the amount of deformation of each of the springs increases, and thus a larger closing force can be provided; by sleeving the atrial appendage with the entire closed loop structure, the atrial appendage can be prevented from escaping from the clip arms after being flattened; and the atrial appendage clip of the present disclosure has a skillful design, has a stable and reliable closing force, is convenient to operate, and is safe and effective.

In the drawings: 1: first clip arm; 11: first cavity; 12: first spring; 13: first pull wire; 14: first wire passing through hole; 15: first fixed pulley; 16: first plug; 17: first mounting groove; 18: pin; 2: second clip arm; 21: second cavity; 22: second spring; 23: second pull wire; 24: second wire passing through hole; 25: second fixed pulley; 26: second plug; 27: second mounting groove; 28: pin; 3: handle shell; 31: button hole; 32: upper shell; 33: lower shell; 34: button; 4: push rod; 5: connection pipe; 6: support base; 61: mounting window; 62: wiring groove; 63: wire passing hole; 7: movable pull wire; 8: fixed pull wire; 9: pipe joint; 10: wire shearing groove; 100: protective sleeve; 20: middle sleeve; 30: radial cutting groove.

DETAILED DESCRIPTION OF THE EMBODIMENTS

Specific implementation manners of the present disclosure will be further described below in detail in combination with accompanying drawings and embodiments. The following embodiments are merely for describing the present disclosure, but are not intended to limit a scope of the present disclosure.

In the description of the present disclosure, it is to be noted that, orientation or position relationships indicated by the terms "center", "longitudinal" "transversal" "upper", "lower", "front", "rear", "left", "right", "vertical", "horizontal", "top", "bottom", "inner", "outer", etc. are based on the orientation or position relationships as shown in the drawings, for ease of the description of the present disclosure and simplifying the description only, rather than indicating or implying that the indicated device or element must have a particular orientation or be constructed and operated in a particular orientation. Therefore, these terms should not be understood as a limitation to the present disclosure. In addition, the terms such as "first", "second" and "third" are merely for a descriptive purpose, and cannot be understood as indicating or implying relative importance, or implicitly indicating the number of the indicated technical features.

In the description of the present disclosure, it is to be noted that, unless otherwise specified and defined, the terms "install", "connected with", "connected to" should be comprehended in a broad sense. For example, these terms may be comprehended as being fixedly connected, detachably connected or integrally connected; mechanically connected or coupled; or directly connected or indirectly connected through an intermediate medium, or in an internal communication between two elements. The specific meanings about the foregoing terms in the present disclosure may be understood by those skilled in the art according to specific circumstances In addition, in the description of the present disclosure, "a plurality of", "multiple" and "multiple groups" means two or more, unless otherwise stated.

The present disclosure provides an atrial appendage clip, which includes a first clip arm and a second clip arm that are symmetrically arranged; a first cavity and a second cavity are respectively provided in the first clip arm and the second clip arm along an axial direction of the first clip arm and the second clip arm; a first spring and a second spring are respectively provided in the first cavity and the second cavity; the first sprig, and the second spring preferably are tension springs; during a process when each of the tension springs is tensed, a tensile length is linearly changed with a stressed tensile force, so that a stable opening or closing force can be provided; the first spring is disposed along a length direction of the first cavity; the second spring is disposed along a length direction of the second cavity; and the first spring is connected with the second clip arm by a first pull wire, and the second spring is connected with the first clip arm by a second pull wire, so as to form a closed loop structure. By sleeving an atrial appendage with the entire closed loop structure, the atrial appendage can be prevented from escaping from the clip arms after being flattened. By disposing the first spring in the first cavity and disposing the second spring in the second cavity, the overall outline dimension of the atrial appendage clip may be reduced, and extrusion and abrasion to a peripheral tissue of the atrial appendage are reduced; moreover, with the increase in the thickness of the atrial appendage, the amount of deformation of each of the springs increases, and thus a larger closing force can be provided. When the first, spring and the second spring are not stressed, i.e., in an original state, the first clip arm and the second clip arm are attached together (i.e., in a closed state) under the action of a pretightening force of the springs. Under the action of an external force, as the first spring and the second spring are stretched or compressed, the first clip arm and the second clip arm are capable of being opened or closed therebetween. For example, when an external tensile force is applied, the first spring and the second spring are tensed, and at this moment, the first clip arm and the second clip arm are opened. When the applied tensile force is removed, the first spring and the second spring are restored to the original state, and at this moment, the first clip arm and the second clip arm are closed and clamped. The atrial appendage clip is placed from an outside of a heart to a root of a left atrial appendage to close the left atrial appendage in the thoracotomy or minimally invasive surgery, the closing force is stable and reliable, the operation is convenient, and the atrial appendage clip is safe and effective. Specifically, the first clip arm and the second clip arm may be made of an implantable metal such as a stainless steel, a cobalt-based alloy, a platiniridium alloy, a nickel-titanium alloy or a magnesium-based alloy. The first spring and the second spring may be made of an implantable metal such as the stainless steel and the nickel-titanium alloy. The first pull wire and the second pull wire may be made of a PET or other polymer materials easily absorbed by a human tissue (such as a material capable of being degraded naturally after a specific service life) or a flexible metal wire so as to reduce the impact on a body of a patient.

In order to describe more clearly, the contents of the present disclosure will be specifically described below with specific embodiments but are not, intended to limit the present disclosure. All contents within a concept of the present disclosure should belong to a scope of protection of the present disclosure.

First Embodiment

Figure 1:
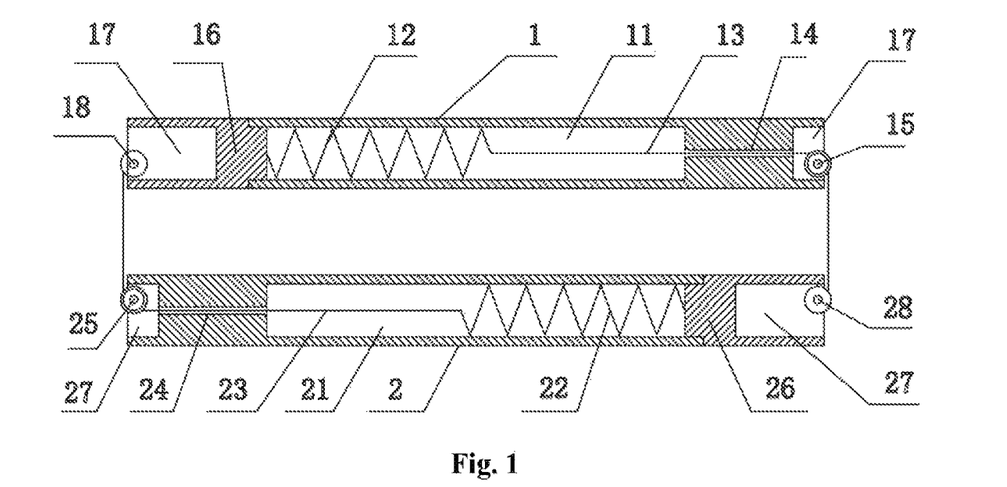
FIG. 1 is a front sectional view of an atrial appendage clip in a first embodiment of the present disclosure.

As shown in FIG. 1, in order to conveniently fix the first spring 12 and the second spring 22, one end of the first spring 12 is connected with an end wall of the first cavity 11, and the other end of the first spring 12 is connected with a corresponding end of the second clip arm 2 by the first pull wire 13, i.e., when the first pull wire 13 turns from an end portion of the first clip arm 1 to the second clip arm 2, the first pull wire 13 is connected with one end, close to the first pull wire 13, of the second clip arm 2; and one end of the second spring 22 is connected with an end wall of the second cavity 21, and the other end of the second spring 22 is connected with a corresponding end of the first clip arm 1 by the second pull wire 23, i.e., when the second pull wire 23 turns from an end portion of the second clip arm 2 to the first clip arm 1, the second pull wire 23 is connected with one end, close to the second pull wire 23, of the first clip arm 1; and thus, the above-mentioned closed loop structure is formed. In addition, the first pull wire 13 and the first spring 12 may be integrated together, e.g., when the first spring 12 is made by using a metal wire, a segment of metal wire not participated in machining is reserved to take as the first pull wire 13. Certainly, the first spring 12 and the first pull wire 13 may also be disposed in a splittable manner and are connected together by a manner of welding, tying and the like. Likewise, the second spring 22 and the second pull wire 23 may also be disposed by adopting a same manner as above-mentioned.

In order to conveniently provide the first pull wire 13 and the second pull wire 23 in a penetration manner, a first wire passing through hole 14 communicating with the first cavity 11 is formed at one end of the first clip arm 1; the first pull wire 13 is connected with a corresponding end of the second clip arm 2 through the first wire passing through hole 14; a second wire passing through hole 24 communicating with the second cavity 21 is formed at one end of the second clip arm 2; and the second pull wire 23 is connected with a corresponding end of the first clip arm 1 through the second wire passing through hole 24.

In order to conveniently install the first spring 12 and the second spring 22, one end, far away from the first wire passing through hole 14, of the first clip arm 1 is provided with a first plug 16; the first plug 16 is configured to block a port of the first cavity 11; the first plug 16 may be connected with the first clip arm 1 together by a manner such as welding or threaded connection; one end of the first spring 12 is connected with an end portion of the first plug 16; and after both are well connected, the first spring 12 is inserted into the first cavity 11 from the port of the first cavity 11, and then the end portion of the first clip arm 1 is blocked by using the first plug 16, so that the first spring is installed in the first cavity 11 conveniently. Likewise, one end, far away from the second wire passing through hole 24, of the second clip arm 2 is provided with a second plug 26; the second plug 26 is configured to block a port of the second cavity 21; one end of the second spring 22 is connected with an end portion of the second plug 26; and after both are well connected, the second spring 22 is inserted into the second cavity 21 from the port of the second cavity 21, and then the end portion of the second clip arm 2 is blocked by using the second plug 26, so that the second spring 22 is installed in the second cavity 21 conveniently.

In order to reduce a friction force of the first pull wire 13 and the second pull wire 23 during movement, one end, close to the first wire passing through hole 14, of the first clip arm 1 is provided with a first fixed pulley 15; one end, close to the second wire passing through hole 24, of the second clip arm 2 is provided with a second fixed pulley 25; the first pull wire 13 is connected with an end portion of the second clip arm 2 by the first fixed pulley 15; further, the first pull wire 13 may be connected with the end portion of the second clip arm 2 by a fixing connection piece such as a pin 28; the second pull wire 23 is connected with an end portion of the first clip arm 1 by the second fixed pulley 25; and correspondingly, the second pull wire 23 may be connected with the end portion of the first clip arm 1 by a fixing connection piece such as a pin 18.

In order to conveniently install the first fixed pulley 15, the second fixed pulley 25 and corresponding fixing connection pieces, two ends of the first clip arm 1 may be respectively provided with first mounting grooves 17; two ends of the second clip arm 2 may be respectively provided with second mounting grooves 27; the first fixed pulley 15 and the pin 18 located at the other end may be correspondingly disposed in the two first mounting grooves 17; and the second fixed pulley 25 and the pin 28 located at the other end may be correspondingly disposed in the two second mounting grooves 27.

Figure 7:
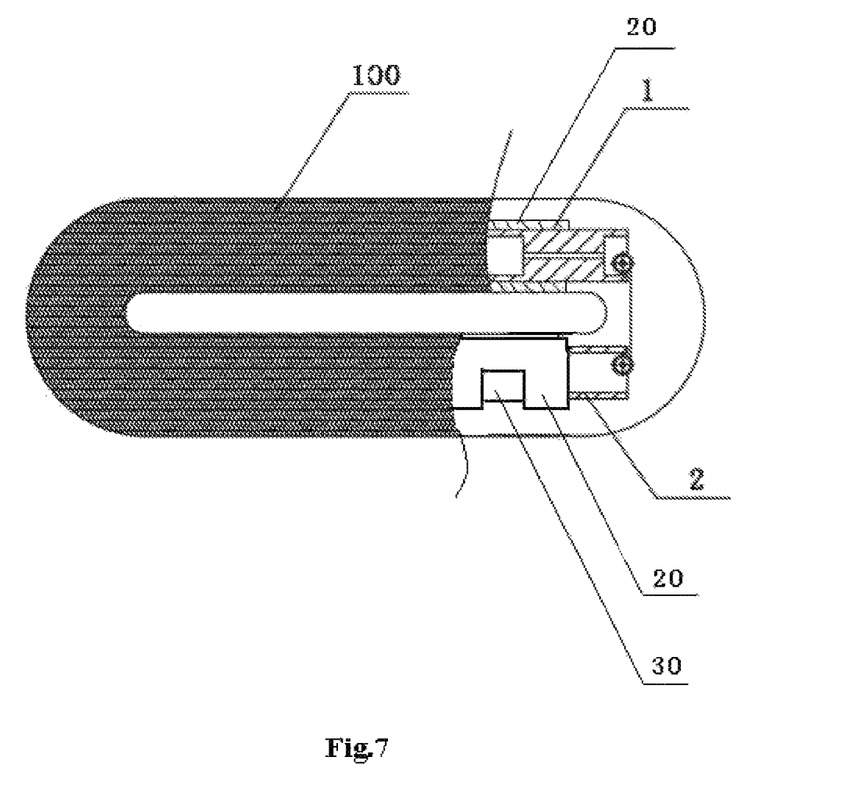
FIG. 7 is a sectional view of an atrial appendage clip (provided with a middle sleeve) in a first embodiment of the present disclosure.

As shown in FIG. 7, middle sleeves 20 are respectively disposed out of the first clip arm 1 and the second clip arm 2 in a sleeving manner; multiple radial cutting grooves 30 are formed out of each of the middle sleeves 20 so as to locate the first pull wire 13 and the second pull wire 23 conveniently; and the middle sleeves 20 may be made of a Polyurethane (PU) or other plastic implantable nonmetals.

Figure 2:
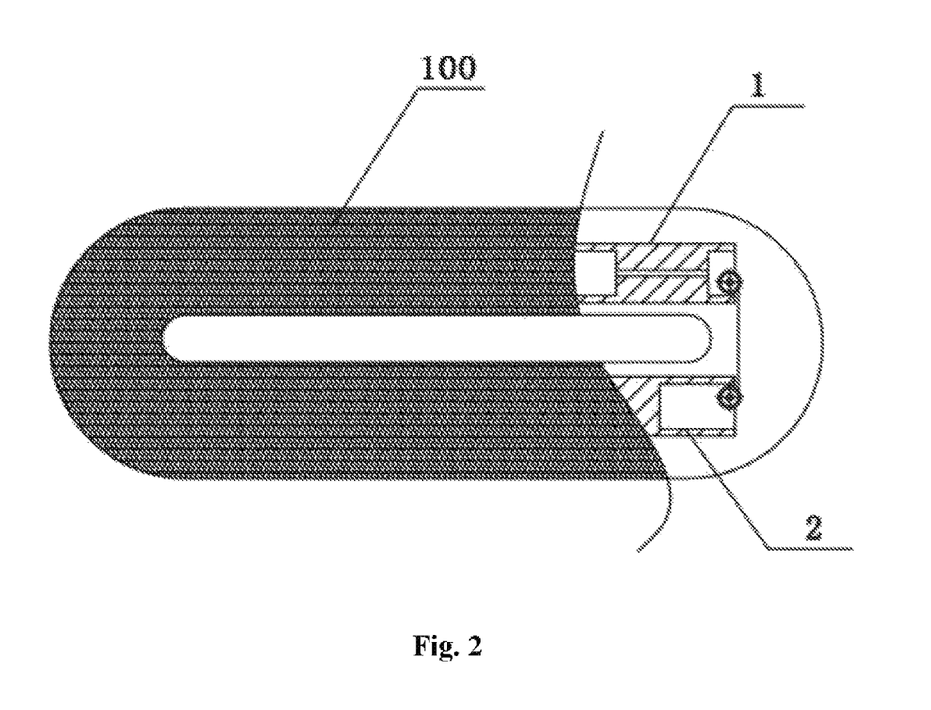
FIG. 2 is a sectional view of an atrial appendage clip (provided with a protective sleeve) in a first embodiment of the present disclosure.

In order to protect a body tissue, and reduce the tissue injury as much as possible, as shown in FIG. 2, a protective sleeve 100 knitted by a braided fabric is further respectively disposed out of the first clip arm 1 and the second clip arm 2 in a sleeving manner; the protective sleeve 100 is of a closed annular shape, is disposed in a sleeving manner sequentially along the first clip arm 1, the first pull wire, the second clip arm 2 and the second pull wire, and is formed into the annular shape by connecting in an end-to-end manner; and the braided fabric may be spun by a polymer material such as a PET (Polyethylene Terephthalate), a PTFE (Polytetrafluoroethylene), a PP (Polypropylene), a velvet, a PGA (Polyglutamic Acid) or a PDO (Propanediol), thereby being beneficial to covering and wrapping a tissue; and therefore, the texture is soft, the stressed area is increased, the pressure of the appliance on the tissue is reduced, and the damage to the body tissue is reduced to minimum.

Second Embodiment

Figure 3:
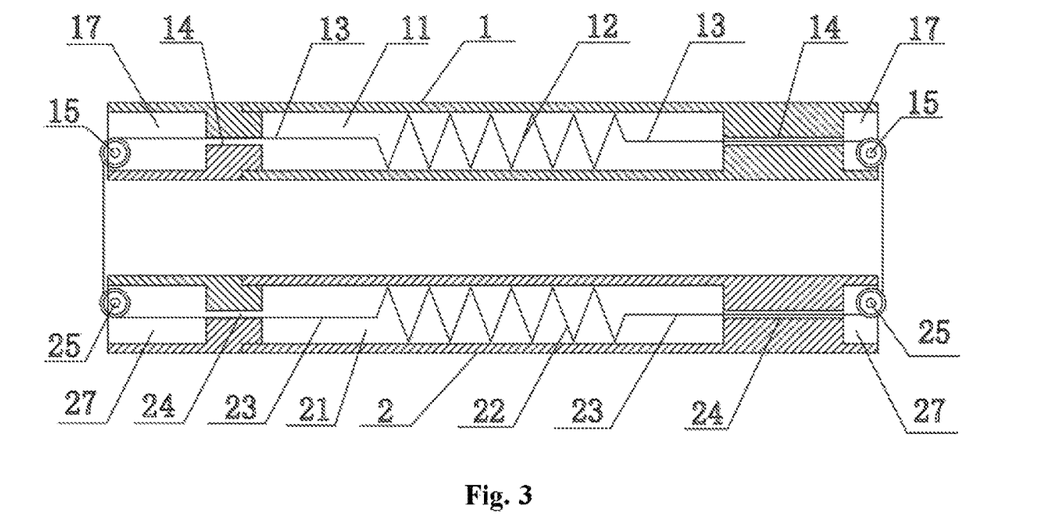
FIG. 3 is a front sectional view of an atrial appendage clip in a second embodiment of the present disclosure.

The difference of the second embodiment from the first embodiment lies in that as shown in FIG. 3, two ends of the first spring 12 are respectively connected to first pull wires 13; two ends of the second spring 22 are respectively connected to second pull wires 23; the first pull wires 13 are correspondingly connected with the second pull wires 23, so that the connection between the first clip arm 1 and the second clip arm 2 is implemented; or two ends of the first spring 12 are fixedly connected with two ends of the second clip arm 2 respectively by the first pull wires 13; and two ends of the second spring 22 are fixedly connected with two ends of the first clip arm 1 respectively by the second pull wires 23.

Herein, first wire passing through holes 14 communicating the first cavity 11 are respectively formed at two ends of the first clip arm; the first pull wires 13 respectively pass through the first wire passing through holes 14; second wire passing through holes 24 communicating the second cavity 21 are respectively formed at two ends of the second clip arm 2; the second pull wires 23 respectively pass through the second wire passing through holes 24; first fixed pulleys 15 are respectively disposed at the two ends of the first clip arm 1; second fixed pulleys 25 are respectively disposed at the two ends of the second clip arm 2; the first pull wires 13 that respectively pass through corresponding first fixed pulleys 15 are correspondingly connected with the second pull wires 23 that respectively pass through corresponding second fixed pulleys 25; or the first pull wires 13 that respectively pass through corresponding first fixed pulleys 15 are connected with the two ends of the second clip arm 2; and the second pull wires 23 that respectively pass through corresponding second fixed pulleys 25 are connected with the two ends of the first clip arm.

Herein, first mounting grooves 17 are respectively formed at two ends of the first clip arm; second mounting grooves 27 are respectively formed at two ends of the second clip arm 2; the first fixed pulleys 15 are respectively and correspondingly disposed in the two first mounting grooves 17; and the second fixed pulleys 25 are respectively and correspondingly disposed in the two second mounting grooves 27.

Third Embodiment

Figure 4:
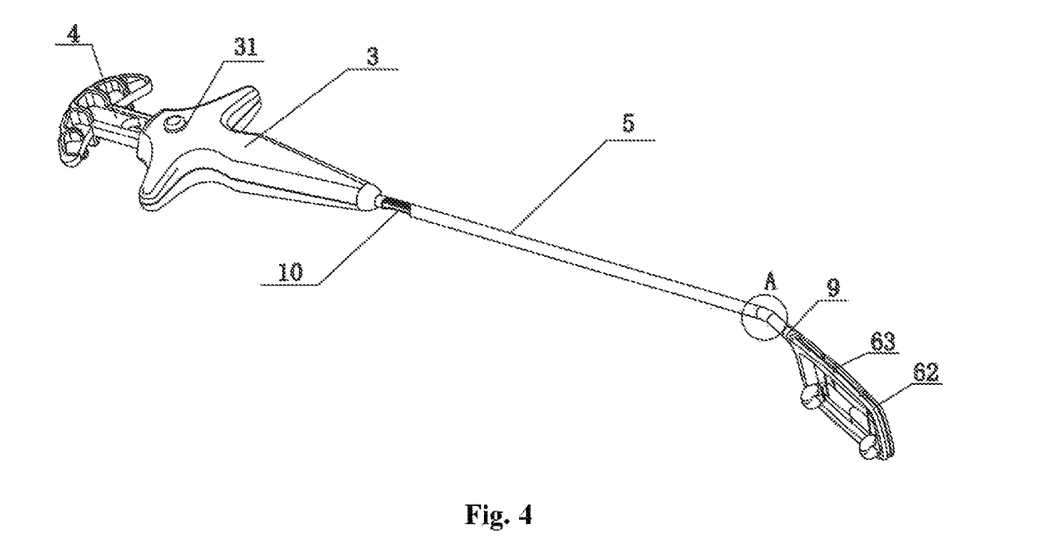
FIG. 4 is an overall structural schematic diagram of an atrial appendage clip delivery system in a third embodiment of the present disclosure.
Figure 5:
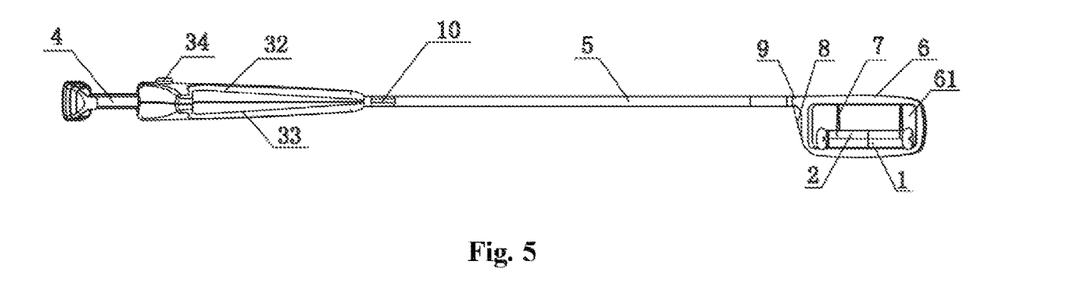
FIG. 5 is a schematic diagram from another perspective of FIG. 4.

As shown in FIG. 4 and FIG. 5, the present disclosure further provides an atrial appendage clip delivery system for delivering the atrial appendage clip in the first embodiment and the second embodiment, which includes a handle shell 3, a push rod 4, a connection pipe 5 and a support base 6; a passage is provided in the handle shell 3 along a length direction of the handle shell 3; and one end of the push rod 4 is located in the passage, and is slidably and cooperatively connected with the passage.

The connection pipe 5 is a hollow pipeline; one end of the connection pipe 5 is connected with the handle shell 3, and the other end of the connection pipe 5 is connected with the support base 6; and the connection pipe 5, the handle shell 3 and the support base 6 keep communicating.

The support base 6 is provided with a mounting window 61. Specifically, the support base 6 preferably is of a mouth shape disposed in a closed loop, and a circular arc chamfering is provided at periphery of the support base 6; the mounting window 61 is a middle through hole of the mouth-shaped support base 6; and the mounting window 61 is configured to mount an atrial appendage clip.

The atrial appendage clip includes a first clip arm 1 and a second clip arm 2 capable of opening in parallel or closing; a spring is connected between the first clip arm 1 and the second clip arm 2, and is configured to provide an elastic force for opening or closing of the first clip arm 1 and the second clip arm 2; the first clip arm 1 or the second clip arm 2 is fixedly connected with an upper side or a lower side of the mounting window 61 by a fixed pull wire 8, so as to fix the first clip arm 1 or the second clip arm 2 at one side of the mounting window 61; the fixed pull wire 8 sequentially passes through the support base 6 and the connection pipe 5, and then is fixedly connected with the handle shell 3; correspondingly, the second clip arm 2 or the first clip arm 1 is movably connected with the lower side or the upper side of the mounting window 61 by a movable pull wire 7; by pulling the movable pull wire 7, the second clip arm 2 or the first clip arm 1 is driven to move toward the other side of the mounting window 61, so that the atrial appendage clip is opened; and specifically, the movable pull wire 7 sequentially passes through the support base 6 and the connection pipe 5, and then is connected with an end portion of the push rod 4. By pulling the push rod 4, the first clip arm 1 and the second clip arm 2 can be separated. By pushing the push rod 4, the first clip arm 1 and the second clip arm 2 can be closed.

As shown in FIG. 4 and FIG. 5, the handle shell 3 is provided with a button 34; the push rod 4 is provided with a sliding groove along an axial direction of the push rod 4; a lower end of the button 34 passes through the sliding groove, and is connected with an elastic reset piece; by pushing the push rod 4 with a palm, the sliding groove moves relative to the button 34; and when the push rod 4 is pushed to a bottom end of the handle shell 3, the button 34 is pressed to compress the elastic reset piece such as a reset, spring (not shown in figure). The push rod 4 is clamped by using a clamping portion of the button, so that position locking between the handle shell 3 and the push rod 4 is implemented; and at this moment, a maximum distance is opened between the first clip arm 1 and the second clip arm 2. Since the position of the push rod is locked, the atrial appendage clip is kept open and then the opened atrial appendage clip may be conveniently placed to a root of an atrial appendage by the atrial appendage clip delivery system; and after a placement position is confirmed, the button 34 is pressed to relieve the position locking of the push rod 4, and the first clip arm 1 and the second clip arm 2 are closed at a root of a left atrial appendage.

As shown in FIG. 2, a pipe joint 9 is disposed at a corner of one side of the support base 6. An upper surface of the pipe joint 9 is flush with an upper surface of the support base. Since a thoracic cavity is very narrow intrinsically, the pipe joint 9 is attached to one side of the support base, thereby being more beneficial to inosculation with a heart tissue, preventing the heart tissue such as an aorta and a pulmonary vein from being pressed, and improving the safety in operation.

For the convenience of wiring, a wiring groove 62 is formed at the periphery of the support base 6; the wiring groove 62 communicates with the pipe joint 9; the support base 6 is connected with the connection pipe 5 by the pipe joint 9; and thus, it is convenient for the movable pull wire 7 and the fixed pull wire 8 to be disposed in the pipe joint 9 in a penetration manner from the wiring groove 62 and to enter the connection pipe 5.

Multiple wire passing holes 63 for passing through the fixed pull wire 8 and the movable pull wire 7 are formed in the wiring groove 62; and further, the wire passing holes 63 are symmetrically formed on upper and lower sidewalls of the mounting window 61.

Figure 6:
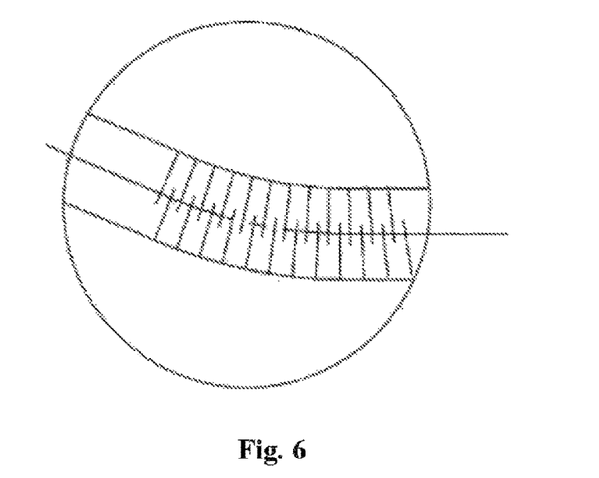
FIG. 6 is a local enlarged diagram of A in FIG. 4.

As shown in FIG. 4 to FIG. 6, the connection pipe 5 may be a segment of complete metal pipe having a predetermined bending angle such as a stainless steel pipe, a nickel-titanium alloy pipe or other medical metal pipes. The predetermined bending angle may be adjusted freely according to a demand, and 360° adjustment without a dead angle may be implemented. Certainly, the connection pipe 5 may, also be a segment of straight pipe; or the connection pipe 5 is formed by multiple segments of connection branch pipes connecting sequentially, where one segment of the connection branch pipe may be provided with a predetermined bending angle, e.g. the predetermined angle is bent artificially; the predetermined bending angle may be adjusted freely according to a demand, and 360° adjustment without a dead angle may be implemented. Certainly, the multiple segments of the connection branch pipes may be all straight pipes; and a wire shearing groove 10 is formed at one end, close to the handle shell 3, of the connection pipe 5 or of one of the connection branch pipes. After the atrial appendage clip is delivered in place, the movable pull wire and the fixed pull wire are sheared in the wire shearing groove, so that the atrial appendage clip is released at the atrial appendage; and by shearing a wire at an outside of the thoracic cavity, an injury to a body of a patient is prevented in a process when the wire is sheared at an inside of the thoracic cavity.

The handle shell 3 includes an upper shell 32 and a lower shell 33. The push rod 4 may be disposed in the lower shell 33 first, and then the upper shall 32 and the lower shell 33 are butted to form the handle shell 3, so that the installation of the push rod 4 is convenient.

The support base 6 may be made of medical polyamide+ 50% glass fiber or other medical nonmetal materials, and may be fixedly connected with the connection pipe 5 by a manner such as sleeving and extruding deformation, gluing and threaded connection.

In the present disclosure, an operation process is as follows: the push rod 4 generates a relative displacement with the handle shell 3 under the action of a pushing force; the movable pull wire 7 fixed on the push rod 4 is moved therewith, and pulls the clip arm at one side of the atrial appendage clip open, so that the two clip arms are opened in parallel; when the push rod 4 is pushed to the bottom end of the handle shell 3, the button 34 is pressed to clamp the push rod 4 and lock the position of the push rod 4; at this moment, a maximum open distance is formed between the clip arms at the two sides of the atrial appendage clip; the atrial appendage clip is stretched into a body of a patient by a wound together with a front end of the atrial appendage clip delivery system; and meanwhile, by virtue of other appliances, the atrial appendage clip sleeves a root of a left atrial appendage; after a placement position is confirmed to be appropriate, the button 34 is pressed manually to relieve the position locking of the push rod 4; at this moment, the clip arms at the two sides of the atrial appendage clip are closed slowly under the action of the springs and the pull wires till the left atrial appendage is attached and is compacted; then, the movable pull wire 7 and the fixed pull wire 8 are sheared at an opening of the wire shearing groove 10; and then, the atrial appendage clip delivery system is taken out from the wound and the rest pull wires winded on the atrial appendage clip are taken out, so that the surgery is implemented completely.

In addition, during the surgery, if a placement direction of the atrial appendage clip cannot meet the surgical demand, the connection pipe may be bent manually by a doctor according to an actual condition so as to achieve a best appropriate angle.

From the above embodiments, it may be seen that the atrial appendage clip of the present disclosure has a skillful structure, is convenient to operate, and is safe and effective; and with the atrial appendage clip delivery system, the atrial appendage clip can be conveniently and reliably placed from the outside of the heart to the root of the left atrial appendage to close or even permanently close the left atrial appendage in a thoracotomy or minimally invasive surgery.

The above are only preferred embodiments of the present disclosure and are not intended to limit the present disclosure. Any modification, equivalent replacement and improvement made within the spirit and principle of the present disclosure should be included in a scope of protection of the present disclosure.

What is claimed is:

1. An atrial appendage clip, comprising a first clip arm and a second clip arm that are symmetrically arranged, wherein a first cavity and a second cavity are respectively provided in the first clip arm and the second clip arm along an axial direction of the first clip arm and the second clip arm; a first spring and a second spring are respectively provided in the first cavity and the second cavity; the first spring is connected with the second clip arm by a first pull wire, and the second spring is connected with the first clip arm by a second pull wire, so as to form a closed loop structure; and as the first spring and the second spring are stretched or compressed, the first clip arm and the second clip arm are capable of being opened or closed, one end of the first spring is connected with an end wall of the first cavity, and the other end of the first spring is connected with a corresponding end of the second clip arm by the first pull wire; and one end of the second spring is connected with an end wall of the second cavity, and the other end of the second spring is connected with a corresponding end of the first clip arm by the second pull wire, wherein a first wire passing through hole communicating with the first cavity is formed at one end of the first clip arm; the first pull wire is connected with the corresponding end of the second clip arm through the first wire passing through hole; a second wire passing through hole communicating with the second cavity is formed at one end of the second clip arm; and the second pull wire is connected with the corresponding end of the first clip arm through the second wire passing through hole, wherein one end, remote from the first wire passing through hole, of the first clip arm is provided with a first plug; a part of the first plug is inserted into the first cavity, the first plug is configured to block a port of the first cavity; an end portion of the first plug forms the end wall of the first cavity and is connected with one end of the first spring; one end, remote from the second wire passing through hole, of the second clip arm is provided with a second plug; a part of the second plug is inserted into the second cavity, the second plug is configured to block a port of the second cavity; an end portion of the second plug forms the end wall of the second cavity and is connected with one end of the second spring.

2. The atrial appendage clip as claimed in claim 1, wherein one end, close to the first wire passing through hole, of the first clip arm is provided with a first fixed pulley; one end, close to the second wire passing through hole, of the second clip arm is provided with a second fixed pulley; the first pull wire is connected with the corresponding end of the second clip arm by the first fixed pulley; and the second pull wire is connected with the corresponding end of the first clip arm by the second fixed pulley.

3. The atrial appendage clip as claimed in claim 2, wherein one end portion of the first clip arm is provided with a first mounting groove for mounting the first fixed pulley; and one end portion of the second clip arm is provided with a second mounting groove for mounting the second fixed pulley.

4. The atrial appendage clip as claimed in claim 1, wherein middle sleeves are respectively disposed about the first clip arm and the second clip arm in a sleeving manner; and a plurality of radial cutting grooves are formed out of each of the middle sleeves.

5. The atrial appendage clip as claimed in claim 4, wherein a protective sleeve knitted by a braided fabric is further respectively disposed about the first clip arm and the second clip arm in a sleeving manner; and the braided fabric is spun by a Polyethylene Terephthalate (PET), a Polytetrafluoroethylene (PTFE), a Polypropylene (PP), a velvet, a Polyglutamic Acid (PGA) or a Propanediol (PDO).

* * * * *